United States Patent [19]

Ohnishi et al.

[11] 4,436,724
[45] Mar. 13, 1984

[54] METHOD OF PRODUCING GAMMA-GLOBULIN FOR INTRAVENOUS INJECTION AND THERAPEUTIC AGENT PRODUCED THEREBY

[75] Inventors: Haruo Ohnishi, Chiba; Hiroshi Kosuzume, Kanagawa; Yasuo Suzuki, Saitama; Ei Mochida, Tokyo, all of Japan

[73] Assignee: Mochida Pharmaceutical Co., Ltd., Tokyo, Japan

[21] Appl. No.: 382,233

[22] Filed: May 26, 1982

[30] Foreign Application Priority Data

May 29, 1981 [JP] Japan .................................. 56-82903

[51] Int. Cl.³ ................................................ C07G 7/00
[52] U.S. Cl. ................................... 424/101; 424/177; 435/68; 435/188; 435/272; 260/112 B
[58] Field of Search .......................... 435/68, 188, 272; 260/112 B; 424/101, 177

[56] References Cited

U.S. PATENT DOCUMENTS 3,553,317  1/1971  Michaelson et al. ............. 435/68 X
4,093,606  6/1978  Coval .................................. 260/112
4,312,949  1/1982  Ahrens ............................... 435/272

OTHER PUBLICATIONS

Methods in Enzymology, vol. XIX pp. 406–421 (1970), Perlmann et al.
Vox Sang. vol. 13, No. 1 (1967), pp. 93–103, Koblet et al. and Steinbuch et al.

Primary Examiner—Howard E. Schain
Attorney, Agent, or Firm—Parkhurst & Oliff

[57] ABSTRACT

A method of producing γ-globulin which can be administered intravenously without adverse reactions and loss of opsonic activity is provided. The method comprises treating γ-globulin with pepsin or uropepsin in a neutral pH range of 6.0 to 7.5. The aggregates in γ-globulin are selectively decomposed by the method of the present invention, while any decomposition of monomer γ-globulin molecule is substantially prevented. A therapeutic agent for intravenous injection which is reduced its anticomplementary activity and is stabilized by adding uropepsin which serves simultaneously as a proteolytic enzyme and a stabilizer, to human γ-globulin. Uropepsinogen can be also as a stabilizer.

35 Claims, 4 Drawing Figures

METHOD OF PRODUCING γ-GLOBULIN FOR INTRAVENOUS INJECTION AND THERAPEUTIC AGENT PRODUCED THEREBY

BACKGROUND OF THE INVENTION

1. Field of the Invention

This invention relates to a method of producing γ-globulin for intravenous injection.

2. Prior Art

Gamma globulin has been widely used for the prophylaxis and therapy of diseases caused by various kinds of virus and bacteria. It has, however, been administered only intramuscularly, since intravenous administration may cause serious adverse reactions, such as a sudden decrease in blood pressure, chill, vomiting, pyrexia, cyanosis or shock. In order to raise the antibody titer in blood quickly, however, it is clinically more advantageous to inject γ-globulin intravenously rather than intramuscularly, since an effective dose of γ-globulin is smaller intravenously than intramuscularly, and the γ-globulin so injected can be utilized more effectively. Intramuscular injection is also undesirable for other reasons; for example, it tends to cause local decomposition of γ-globulin at the site of injection, while intramuscular injection of a large quantity of γ-globulin may cause local pain or induration of the muscle.

The process of the adverse reactions caused by intravenous administration of γ-globulin is generally explained as follows: some part of γ-globulin molecules aggregate during its purification, and these aggregates cause nonspecific complement activation in the current which is different from antigen-antibody reaction. Various attempts have, therefore, been made to provide a method of producing γ-globulin which can be administered intravenously without causing activation of complement, i.e., γ-globulin having a reduced anticomplementary activity, which does not cause any adverse reactions. Several methods have been proposed for producing such γ-globulin, for example, (1) partial degradation of γ-globulin with a proteolytic enzyme (H. Koblet et al., Vox Sang., 13, 92 (1967), and L. A. Hanson et al., Int. Arch. Allergy, 31, 380 (1967)), (2) chemical modification of γ-globulin (Vox Sang., 28, 422 (1975)), (3) removal of the aggregates from γ-globulin (U.S. Pat. No. 4,093,606, and Japanese Patent Laid-Open Nos. 81519/74 and 101516/74), (4) addition of one or more substances for preventing regeneration of aggregates in γ-globulin which has been freed from aggregates (Japanese Patent Laid-Open Nos. 91321/76 and 47515/78), or (5) addition of one or more substances which can dissociate the aggregates in γ-globulin and at the same time can prevent regeneration of aggregates in it (Japanese Patent Laid-Open No. 20124/79). Among these methods, the degradation of γ-globulin with a proteolytic enzyme such as pepsin or plasmin to reduce its anticomplementary activity was first proposed and has long been employed as an effective method for practical purposes. This method, however, lowers the opsonic activity of γ-globulins since those enzymes bring about partial decomposition of its molecular structure. Moreover, if pepsin is used as a proteolytic enzyme, the resulting γ-globulin is known to possess an extremely short half-life in the current.

SUMMARY OF THE INVENTION

The inventors of this invention have conducted extensive research to provide a method of producing γ-globulin which is suitable for intravenous administration because of its sufficient opsonic activity and long half-life in the current by treating γ-globulin with a proteolytic enzyme. As a result, they have surprisingly discovered that if γ-globulin is reacted with pepsin in a neutral pH range of 6.0 to 7.5, γ-globulin aggregates can be selectively decomposed or dissociated, while monomer γ-globulin molecules are scarcely affected.

The main object of the present invention is, therefore, to provide a method of producing γ-globulin suitable for intravenous injection by an enzyme treatment.

More specifically, the object of the present invention is to provide a method of reducing anticomplementary activity of γ-globulin by selective decomposition of the aggregates without causing the decomposition of monomer γ-globulin molecules, namely without losing its opsonic activity, thus enabling production of γ-globulin which is suitable for intravenous injection because of its negligible adverse reactions, high antibody titer and long half-life in the current.

Still further object of the present invention is to provide a therapeutic agent for intravenous injection which is reduced its anticomplementary activity and is stabilized by adding uropepsin which serves simultaneously as a proteolytic enzyme and a stabilizer, to human γ-globulin.

Still further object of the present invention is to provide a therapeutic agent for intravenous injection which is reduced its anticomplementary activity and is stabilized by adding uropepsinogen as a stabilizer to human γ-globulin whose anticomplementary activity has been reduced.

DETAILED DESCRIPTION OF THE INVENTION

This invention is usually carried out in the manner as follows. A solution of γ-globulin which is prepared by a known method is adjusted to a neutral pH range of 6.0 to 7.5, preferably from 6.5 to 7.0, and it is then treated with an appropriate quantity of pepsin or uropepsin at a temperature range of 25° C. to 37° C. for 12 to 96 hours.

It is well known that the optimum pH of pepsin is usually in the range of 2.0 to 3.0, and that if γ-globulin is reacted with pepsin in such a pH range, its Fc portion is removed, and only its F(ab')$_2$ portion will be retained, thereby losing the opsonic activity of the γ-globulin. According to this invention, however, pepsin is reacted to γ-globulin in the neutral pH range of 6.0 to 7.5 that it may act selectively only upon γ-globulin aggregates, and therefore it scarcely affects monomer γ-globulin molecules. It is, therefore, possible to obtain γ-globulin of a low anticomplementary activity without decreasing the opsonic activity of monomer γ-globulin. A pH exceeding 7.5 should not be used, since it inactivates the enzyme activity of pepsin. The term "pepsin" is intended in this specification to mean both pepsin and uropepsin.

The present invention will be further explained by the following experimental examples:

EXPERIMENT 1

Figure 1A:
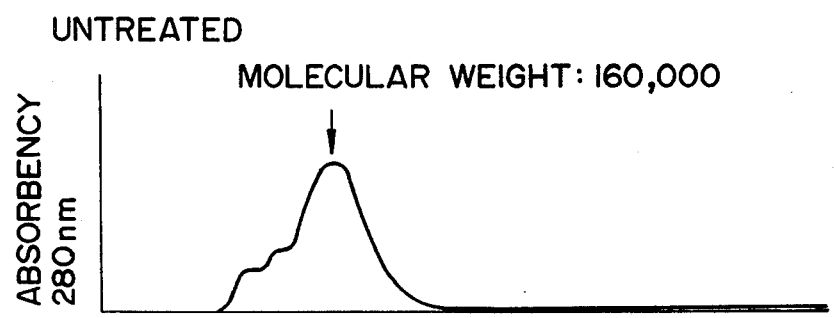
FIGS. 1A, B are a pair of graphs comparing the gel filtration patterns of untreated and treated γ-globulin with immobilized uropepsin at pH 7.0 in EXPERIMENT 1, and FIGS. 2A, B are a pair of graphs comparing the gel filtration patterns of untreated and treated γ-globulin with immobilized uropepsin at pH 4.5.
Figure 1B:
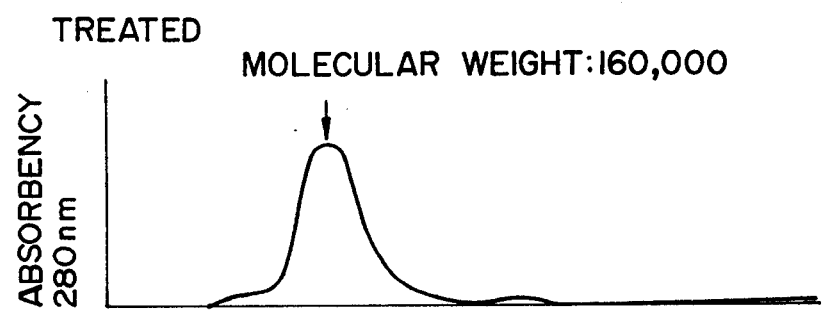

Gamma globulin was obtained by Cohn fractionation with ethanol, and subjected to a gel filtration on Sephadex ®G-200. In addition to a main peak corresponding to γ-globulin, the product showed two peaks which correspond to higher molecular weights, as shown in FIG. 1. The γ-globulin from the gel filtration was treated with uropepsin as in EXAMPLE 1, which will be described later. No change in the main peak of the resulting product was observed when it was subjected again to the same gel filtration, while the other two peaks, which are considered to be the indications of the presence of aggregates, were lowered considerably. The γ-globulin showed an anticomplementary activity not exceeding $10CH_{50}/50$ mg γ-globulin after treatment with the enzyme. This value fully satisifies the γ-globulin requirements for intravenous injection.

Figure 2A:
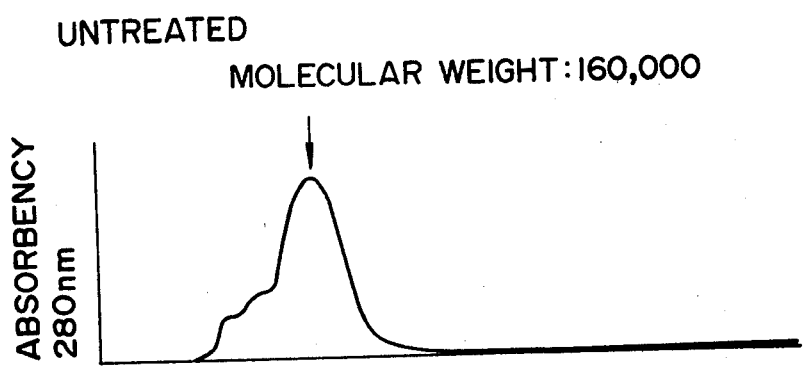
Figure 2B:
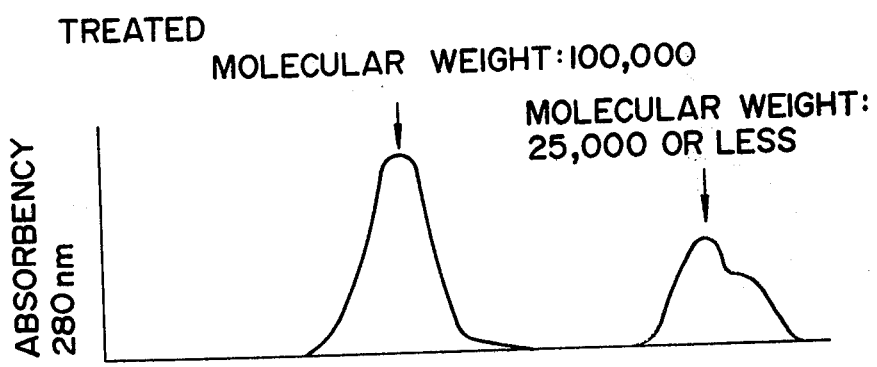

A similar experiment was conducted by an ordinary method at pH 4.5. Although the product showed a sufficiently low anticomplementary activity, the gel filtration pattern indicated a molecular distribution generally shifting to lower molecular weight (FIG. 2) because of the decomposition of monomer γ-globulin molecules as well as γ-globulin aggregates.

EXPERIMENT 2—Opsonic Activity

The opsonic activity of γ-globulin which has been treated with pepsin as in EXAMPLES 1 and 3 (which will be described later) was examined in accordance with the method of Young et al. (L. S. Young et al., The Journal of Infectious Diseases, 126, 257 (1972)).

More specifically, 0.6 ml of serum which has been absorbed by mixing with E. coli (NIHJC-2) at 4° C. and 0.1 ml of γ-globulin solution to be tested were mixed with 0.2 ml of a suspension of human neutrophiles ($10^7$ cells per milliliter) and 0.1 ml of the suspension of E. coli ($2 \times 10^6$ cells per milliliter). The mixture was incubated at 37° C. for two hours, and thereafter cultured on an ordinary agar medium. The number of surviving bacteria was counted. The results are shown in TABLE 1.

The γ-globulin treated with human uropepsin or swine pepsin at pH 7.0 showed an opsonic activity comparable to that of human monomer γ-globulin purified from human serum in accordance with the method of Sober et al. (Sober et al., J. Am. Chem. Soc., 78, 756 (1956)). To the contrary, the γ-globulin treated with human uropepsin at pH 4.5 showed only little opsonic activity.

TABLE 1

| | | Number of surviving bacteria in 1 ml of the reacted solution |
|---|---|---|
| Control | | $1.8 \times 10^5$ |
| γ-globulin treated with human uropepsin at pH 7.0 | 3 mg/ml | $1.1 \times 10^4$ |
| | 1 mg/ml | $4.0 \times 10^4$ |
| | 0.3 mg/ml | $8.0 \times 10^4$ |
| γ-globulin treated with swine pepsin at pH 7.0 | 3 mg/ml | $1.3 \times 10^4$ |
| Human monomer γ-globulin | 3 mg/ml | $1.2 \times 10^4$ |
| γ-globulin treated with human uropepsin at pH 4.5 | 3 mg/ml | $1.7 \times 10^5$ |

EXPERIMENT 3—Comparison of Half-Life In Vivo

A comparative test was carried out using γ-globulin obtained by the treatment with human uropepesin at pH 7.0 and human monomer γ-globulin of groups each consisting of six New Zealand white-strain male rabbits weighting 2 to 2.5 kg. An intravenous injection of 50 mg of γ-globulin labelled with radioactive iodine ($^{125}I$) was given to each rabbit. Blood was collected 3, 6, 12, 24, 36, 48, 60, 72 and 96 hours after the injection, and its radioactivity was monitored and the half-life was calculated. The results are shown in TABLE 2.

The γ-globulin treated with human uropepsin at pH 7.0 showed a half-life which was comparable to that of human monomer γ-globulin.

TABLE 2

| γ-globulin | Half-life (hours) |
|---|---|
| γ-globulin treated with human uropepsin at pH 7.0 | $37.2 \pm 3.2$ |
| Human monomer γ-globulin | $36.5 \pm 4.5$ |

EXPERIMENT 4—Action for the Infection of Pseudomonas Aeruginosa on Mice

Prophylactic actions against the infection of *Pseudomonas aeruginosa* were compared for γ-globulin obtained by treatment with human uropepsin at pH 7.0 and human monomer γ-globulin on groups each consisting of 10 male ddY mice weighing 18 to 20 g in accordance with the method of Haranaka et al. (Haranaka et al., The Journal of the Japanese Association for Infectious Diseases, 52,490 (1978)). A suspension of $5 \times 10^6$ bacteria in 4% mucin was innoculated intraperitoneally to each mouse which had previously been given a subcutaneous administration of γ-globulin obtained by treatment with human uropepsin at pH 7.0 or human momoner γ-globulin in an amount of 30 mg/kg. After four days, their survival rates were examined. The results are shown in Table 3.

The survival rate of the animals which had been given the administration of γ-globulin treated with human uropepsin at pH 7.0 was equal to that of the animals which had been given the administration of human monomer γ-globulin, and the rate was significantly higher than that of the control group which had not been given the administration of γ-globulin.

TABLE 3

| | Survival (%) |
|---|---|
| Control group | 0 |
| Mice to which the γ-globulin treated with human uropepsin at pH 7.0 had been administered | 70** |
| Mice to which human monomer γ-globulin had been administered | 70** |

**$P < 0.01$

Although, according to this invention, it is most desirable to use human pepsin, it is also possible to use pepsin obtained from other sources. It is possible to use gastric pepsin, and also urinary pepsin, i.e., uropepsin.

For example, uropepsin can be purified from human urine by the method of Seijffers (Seijffers, Amer. J. Physiol., 206, 1106 (1964)).

As a non-limiting example, human urine is passed through a DEAE-cellulose column equilibrated with 0.1 M acetate buffer solution (pH 5.3) so as to have the uropepsinogen adsorbed on the column. The uropepsinogen is then eluted with the same buffer solution containing 0.3 M sodium chloride. The eluate is concentrated, then further purified by gel chromatography using Sephadex G-100, and subjected to an acid treatment.

Gastric pepsin can be prepared, e.g., according to the method of Tang et al. (Tang et al., Method in Enzymology, 19, 406 (1970)), by passing human gastric juice through a column of Amberlite IRC-50 which has been equilibrated with 0.2 M sodium citrate buffer (pH 3.0). After the subsequent washing of the column with 0.2 M citrate buffer (pH 3.8), adsorbed pepsin is eluted with 0.2 M citrate buffer (pH 4.2). Gastric pepsin is obtained from the eluate after subjecting it to a further chromatography in the same condition. It is also possible to use pepsin of other animal origin, e.g., swine.

Pepsin can also be prepared from cultured tumour cells fused with cells producing pepsin, or it can also be prepared by genetic technology. For example, it can be prepared on a large scale by the culture of bacteria such as E. coli. which has been subjected to recombination of a complementary DNA transcribed from a messenger RNA template for pepsin with a reverse transcriptase.

Pepsin can be used either in a soluble form, or in an immobilized form. For example, pepsin may be immobilized on an appropriate carrier such as an insoluble carrier consisting of Sepharose ®, Sephadex ®, cellulose, or the like. The use of immobilized pepsin facilitates its removal from γ-globulin after the enzyme treatment. The immobilized form is particularly desired when the pepsin is not of human origin, since the contamination of pepsin in the γ-globulin preparation can be avoided effectively.

Gamma globulin is treated with pepsin at a temperature range of 25° C. to 37° C. at which an ordinary enzymic reaction takes place.

The reaction time may usually be in the range of 12 to 96 hours, depending on the level of anticomplementary activity of γ-globulin as a raw material, the activity of employed pepsin, and the amount of γ-globulin and pepsin.

Although batch methods may be employed for treating γ-globulin with immobilized pepsin, it is more efficient and desirable to circulate a γ-globulin solution through a column containing immobilized pepsin. If pepsin is used in a soluble form, it is necessary to raise the pH of the solution, for example to pH 8.0 to 8.5, to inactivate the pepsin after the reaction. If required, particularly when the pepsin used is not of human origin, the pepsin can be separated from γ-globulin by an appropriate method such as gel filtration. It is advantageous to use immobilized pepsin, since it can be separated very easily and completely.

Gamma-globulin treated with pepsin as described above has a level of anticomplementary activity not exceeding a standard value of $20CH_{50}/50$ mg γ-globulin. An injection may be prepared from the γ-globulin of the present invention by an ordinary method. While the injection may be in the form of a liquid, it is more preferred from the standpoint of its stability to make a freeze-dried preparation which can be dissolved when it is used. It is preferable to add one or more stabilizers, such as human serum albumin, glycin, sorbitol or gelatin. Gumma-globulin preparation of higher stability can also be prepared by adding human uropepsin or uropepsinogen as a stabilizer in the amount of 0.01 to 5%, preferably, 0.1 to 1%.

The treatment of γ-globulin with uropepsin is generally conducted as mentioned above, but it may also be conducted as follows. Gamma-globulin with high level of anticomplementary activity is placed in vessels, for example, vials at a given amount; uropepsin is added thereto and is incubated to lower the level of anticomplementary activity; and then, the mixture is lyophilized as it is without removing uropepsin. In this treatment, uropepsin serves also as a stabilizer.

Although it is especially useful for producing intravenously injectable human γ-globulin, the method of the present invention is applicable to γ-globulin of any animal origin.

The invention will now be described more specifically with reference to examples. It is, however, to be understood that the present invention is not necessarily limited to these examples, since the reaction temperature, flow rate, duration of the enzyme treatment, concentration of γ-globulin, and other factors relate to one another, and for this reason a variety of other combinations is possible to lower the anticomplementary activity of γ-globulin.

EXAMPLE 1

Preparation of Uropepsinogen

One hundred liters of human urine were concentrated to about one-thousandth of their initial volume using a pressure ultrafiltration instrument (Pellicon ®, Millipore Co., and Diaflo ®, Amicon Co.) with a cut off of 10,000 daltons. One hundred milliliters of the concentrated urine were applied to a DEAE-cellulose (Whatman Co.) column (2.5×20 cm) equilibrated with 0.1 M acetate buffer (pH 6.0) and eluted with the same buffer containing 0.3 M sodium chloride. The eluate was concentrated to about 100 ml by ultrafiltration and subjected to dialysis. The dialyzed solution was then applied to a DEAE-Sepharose (Pharmacia Co.) column (2.5×20 cm) under the same conditions described above. The eluted fraction was concentrated to about 10 ml, and applied to a Sephadex G-100 gel filtration column (2.5×90 cm) for further purification. About 80 ml of the solution thus obtained was lyophilized to give about 20 mg of the uropepsinogen.

EXAMPLE 2

Preparation of Swine Pepsin

Five kilograms of swine gastric mucosa was homogenized in a blender and the homogenate was extracted with 10 l. of 0.02 M phosphate buffer (pH 6.9) for one hour with gentle stirring. The extract was passed through a column (10×60 cm) of DEAE-cellulose equilibrated with the same buffer and then, the adsorbed pepsinogen was eluted with 0.3 M NaCl in the same buffer. The eluate was concentrated to 80 ml by ultrafiltration through a Diaflo membrane (Amicon ®). The concentrated solution was acidified to pH 2.0 with 1 N HCl and kept at 37° C. for 10 minutes. Immediately after that, the pH of the solution was raised to pH 4.40 by adding 4 N acetate buffer (pH 5.0). The solution was applied on a column (5×90 cm) of Sephadex ®G-100 equilibrated with physiological saline solution and the development was carried out with the same solution. The fractions containing swine pepsin were collected, and about 500 mg of pepsin were obtained.

EXAMPLE 3

(a) Preparation of Immobilized Uropepsin

Distilled water was added to 10 ml of Sepharose ®4B to make its volume 20 ml. Its pH value was adjusted to 11.0 with 6 N sodium hydroxide solution. Then, 20 ml of 2.5% cyanogen bromide solution were added, and the pH of the suspension was maintained in the range of 11.0 to 11.5 by the addition of 6 N sodium hydroxide solution for 30 minutes, while the temperature of the solution was kept at 16° C. Immediately after that, the Sepharose ®4B was carefully washed with distilled water and 0.1 M sodium hydrogen carbonate solution, each of which had been cooled to 5° C., to remove cyanogen bromide. The Sepharose ®4B was suspended in a 0.1 M sodium hydrogen carbonate solution to form 20 ml of a suspension. Added into the suspension was 10 mg of uropepsinogen purified from human urine by the Seijffers' method. They were reacted at 5° C. for 16 hours while the suspension was gently stirred, whereby immobilized uropepsinogen was prepared. The immobilized uropepsinogen was activated for 10 minutes at pH 2.0 to convert it to immobilized uropepsin. After the immobilized uropepsin had been washed with distilled water, 0.01 M phosphate buffer solution (pH 7.0) containing 0.15 M sodium chloride was added to form 20 ml of a suspension.

(b) Preparation of Gamma Globulin Treated with Uropepsin at pH 7.0

A column was filled with 1.2 ml of the immobilized uropepsin prepared in (a) above, equilibrated with 0.01 M phosphate buffer solution (pH 7.0), and kept at a temperature of 37° C. Twenty milliliters of a solution containing 110 mg/ml of γ-globulin were circulated through the column at a flow rate of 6 ml per hour, and reacted with the uropepsin for 96 hours. Tables 4 and 5 respectively show the changes in the level of anticomplementary activity of γ-globulin after different durations of uropepsin treatment and the properties of the resulting γ-globulin.

TABLE 4

| | Reaction time (hours) | | | | |
|---|---|---|---|---|---|
| | 0 | 12 | 24 | 48 | 96 |
| Anticomplementary activity $CH_{50}/50$ mg γ-globulin | 86.7 | 65.4 | 22.9 | 16.7 | 10.0 |

TABLE 5

| | Untreated | Uropepsin-treated |
|---|---|---|
| Purity (Electrophoresis) | 7S 90% Larger than 7S-10% | 7S 98% Larger than 7S-2% |
| Anticomplementary activity | 87 $CH_{50}/50$ mg γ-globulin | 10 $CH_{50}/50$ mg γ-globulin |
| Antibody titer* | Influenza virus 0.11 mg/ml Coxsackie virus 0.31 mg/ml Klebsiella 0.63 mg/ml E. coli 0.63 mg/ml | Influenza virus 0.11 mg/ml Coxsackie virus 0.31 mg/ml Klebsiella 0.63 mg/ml E. coli 0.63 mg/ml |
| Opsonic activity** | 100 | 100 |

*Minimum concentration at which γ-globulin causes bacterial agglutination
**Relative value when the opsonic activity of untreated γ-globulin was made as 100.

EXAMPLE 4

Fifty milligrams of γ-globulin obtained from human placenta (see for example, Japanese patent publication No. 48-7762), and 1 mg of human uropepsin were dissolved in 5 ml of 0.01 M phosphate buffer (pH 6.5) containing 0.15 M sodium chloride. After they had been reacted at 37° C. for 60 minutes, the reaction was stopped by adding 0.1 N sodium hydroxide solution. The properties of the γ-globulin obtained are shown in TABLE 6.

TABLE 6

| | Untreated | Uropepsin-treated |
|---|---|---|
| Anticomplementary activity | 60 $CH_{50}/50$ mg γ-globulin | 11 $CH_{50}/50$ mg γ-globulin |
| Antibody titer* | Influenza virus 0.11 mg/ml E. coli 0.63 mg/ml | Influenza virus 0.11 mg/ml E. coli 0.63 mg/ml |
| Opsonic activity** | 100 | 100 |

*Minimun concentration at which γ-globulin causes bacterial agglutination
**Relative value when the opsonic activity of untreated γ-globulin was made as 100.

EXAMPLE 5

Two milliliters of immobilized swine pepsin-Sepharose ® obtained in accordance with the procedures of EXAMPLE 1 were placed in a column, equilibrated with 0.01 M phosphate buffer solution (pH 6.5), and kept at a temperature of 30° C. Then, 20 ml of a solution containing 100 mg/ml of γ-globulin were reacted for 48 hours by circulating through the column at a flow rate of 10 ml per hour. The properties of the resulting γ-globulin are shown in TABLE 7.

TABLE 7

| | Untreated | Pepsin-treated |
|---|---|---|
| Anticomplementary activity | 65 $CH_{50}/50$ mg γ-globulin | 13 $CH_{50}/50$ mg γ-globulin |
| Antibody titer* | Influenza virus 0.11 mg/ml Coxsackie virus 0.31 mg/ml Klebsiella 0.63 mg/ml E. coli 0.63 mg/ml | Influenza virus 0.11 mg/ml Coxsackie virus 0.31 mg/ml Klebsiella 0.63 mg/ml E. coli 0.63 mg/ml |
| Opsonic activity** | 100 | 75 |

*Minimum concentration at which γ-globulin causes bacterial agglutination
**Relative value when the opsonic activity of untreated γ-globulin was made as 100.

EXAMPLE 6

Ten ml of uropepsin solution of 1.5 mg/ml were respectively added to 1,000 vials each containing 500 mg of γ-globulin (31$CH_{50}$/50 mg γ-globulin), and the mixtures were incubated at 37° C. for 96 hours at pH 6.5. After the completion of the incubation, the mixtures were lyophilized as they were without removing uropepsin. The level of anticomplementary activity of the treated γ-globulin was 18$CH_{50}$/50 mg γ-globulin.

EXAMPLE 7

One g of uropepsin was added, as a stabilizer, to 250 g of γ-globulin (16$CH_{50}$/50 mg γ-globulin), and the mixture was dissolved in 5 l of 0.9% physiological saline solution. After the solution was sterilized by filtration, each 10 ml of the solution were placed in vials and lyophilized. The results in the measurement of the level of anticomplementary activity after the storage at 4° C. for three months are shown in Table 8.

TABLE 8

| Stabilizer | Level of anticomplementary activity before storage CH$_{50}$/50 mg γ-globulin | Level of anticomplementary activity after storage CH$_{50}$/50 mg γ-globulin |
| --- | --- | --- |
| Non | 16 | 48 |
| uropepsin | 16 | 14 |

What is claimed is:

1. A method of producing γ-globulin for intravenous injection, which comprises treating γ-globulin with an enzyme, selected from pepsin and uropepsin, in a pH range of 6.0 to 7.5.

2. A method according to claim 1, wherein said γ-globulin is of human origin.

3. A method according to claim 1 or claim 2, wherein the pH range is from 6.5 to 7.0.

4. A method according to claim 1 or claim 2, wherein the enzyme is of human origin.

5. A method according to claim 3, wherein the enzyme is of human origin.

6. A method according to claim 1 or claim 2, wherein the enzyme is of non-human origin.

7. A method according to claim 3, wherein the enzyme is of non-human origin.

8. A method according to claim 4, wherein the enzyme is used in a soluble form.

9. A method according to claim 5, wherein the enzyme is used in a soluble form.

10. A method according to claim 4, wherein the enzyme is used in an immobilized form.

11. A method according to claim 5, wherein the enzyme is used in an immobilized form.

12. A method according to claim 6, wherein the enzyme is used in an immobilized form.

13. A method according to claim 7, wherein the enzyme is used in an immobilized form.

14. A method according to claim 1 or 2, wherein γ-globulin is treated with the enzyme at a temperature range of 25° C. to 37° C. for 12 to 96 hours.

15. A method according to claim 3, wherein γ-globulin is treated with the enzyme at a temperature range of 25° C. to 37° C. for 12 to 96 hours.

16. A method according to claim 4, wherein γ-globulin is treated with the enzyme at a temperature range of 25° C. to 37° C. for 12 to 96 hours.

17. A method according to claim 5, wherein γ-globulin is treated with the enzyme at a temperature range of 25° C. to 37° C. for 12 to 96 hours.

18. A method according to claim 6, wherein γ-globulin is treated with the enzyme at a temperature range of 25° C. to 37° C. for 12 to 96 hours.

19. A method according to claim 7, wherein γ-globulin is treated with the enzyme at a temperature range of 25° C. to 37° C. for 12 to 96 hours.

20. A method according to claim 8, wherein γ-globulin is treated with the enzyme at a temperature range of 25° C. to 37° C. for 12 to 96 hours.

21. A method according to claim 9, wherein γ-globulin is treated with the enzyme at a temperature range of 25° C. to 37° C. for 12 to 96 hours.

22. A method according to claim 10, wherein γ-globulin is treated with the enzyme at a temperature range of 25° C. to 37° C. for 12 to 96 hours.

23. A method according to claim 11, wherein γ-globulin is treated with the enzyme at a temperature range of 25° C. to 37° C. for 12 to 96 hours.

24. A method according to claim 12, wherein γ-globulin is treated with the enzyme at a temperature range of 25° C. to 37° C. for 12 to 96 hours.

25. A method according to claim 13, wherein γ-globulin is treated with the enzyme at a temperature range of 25° C. to 37° C. for 12 to 96 hours.

26. A method according to claim 10, wherein said γ-globulin is treated with the enzyme by circulating the γ-globulin solution through a column which has been filled with the enzyme in an immobilized form.

27. A method according to claim 11, wherein said γ-globulin is treated with the enzyme by circulating the γ-globulin solution through a column which has been filled with the enzyme in an immobilized form.

28. A method according to claim 12, wherein said γ-globulin is treated with the enzyme by circulating the γ-globulin solution through a column which has been filled with the enzyme in an immobilized form.

29. A method according to claim 13, wherein said γ-globulin is treated with the enzyme by circulating the γ-globulin solution through a column which has been filled with the enzyme in an immobilized form.

30. A therapeutic agent for intravenous injection comprising γ-globulin, and a stabilizer selected from human uropepsin and human uropepsinogen, said therapeutic agent having a pH in the range of 6.0–7.5.

31. A therapeutic agent for intravenous injection according to claim 30, wherein γ-globulin is human γ-globulin.

32. A therapeutic agent for intravenous injection according to claim 30 or 31 containing 0.01 to 5% of human uropepsin or human uropepsinogen.

33. A therapeutic agent for intravenous injection according to claim 32 containing 0.1 to 1% of human uropepsin or uropepsinogen.

34. A therapeutic agent for intravenous injection, comprising γ-globulin and a stabilizing effective amount of a stabilizer selected from human uropepsin and human uropepsinogen.

35. A therapeutic agent for intravenous injection comprising γ-globulin treated with an enzyme, said enzyme being selected from pepsin and uropepsin, in a pH range of 6.0 to 7.5.

* * * * *